US009080197B2

(12) United States Patent
Tsuji et al.

(10) Patent No.: US 9,080,197 B2
(45) Date of Patent: Jul. 14, 2015

(54) EQUOL LEVEL REGULATOR

(75) Inventors: Hirokazu Tsuji, Minato-ku (JP); Koji Nomoto, Minato-ku (JP); Hideyuki Akaza, Shinjyuku-ku (JP)

(73) Assignee: KABUSHIKI KAISHA YAKULT HONSHA, Minato-ku (JP)

(*) Notice: Subject to any disclaimer, the term of this patent is extended or adjusted under 35 U.S.C. 154(b) by 281 days.

(21) Appl. No.: 12/092,355

(22) PCT Filed: Nov. 2, 2006

(86) PCT No.: PCT/JP2006/321963
§ 371 (c)(1),
(2), (4) Date: May 1, 2008

(87) PCT Pub. No.: WO2007/052740
PCT Pub. Date: May 10, 2007

(65) Prior Publication Data
US 2009/0253643 A1 Oct. 8, 2009

(30) Foreign Application Priority Data

Nov. 2, 2005 (JP) ................................. 2005-319548

(51) Int. Cl.
| A61K 31/7004 | (2006.01) |
| A61K 31/702 | (2006.01) |
| A61K 31/047 | (2006.01) |
| A61P 5/00 | (2006.01) |
| C12Q 1/04 | (2006.01) |
| A23L 1/09 | (2006.01) |
| A23L 1/236 | (2006.01) |
| A61K 31/7016 | (2006.01) |

(52) U.S. Cl.
CPC ... *C12Q 1/04* (2013.01); *A23L 1/09* (2013.01); *A23L 1/097* (2013.01); *A23L 1/2363* (2013.01); *A61K 31/047* (2013.01); *A61K 31/702* (2013.01); *A61K 31/7004* (2013.01); *A61K 31/7016* (2013.01)

(58) Field of Classification Search
None
See application file for complete search history.

(56) References Cited

U.S. PATENT DOCUMENTS 6,716,424 B1 4/2004 Uchiyama et al.

FOREIGN PATENT DOCUMENTS

| JP | 62 220198 | 9/1987 |
| JP | 2003 310177 | 11/2003 |
| WO | 99 07392 | 2/1999 |
| WO | WO 99/07392 | 2/1999 |
| WO | WO 00/56276 A1 | 9/2000 |
| WO | 2005 000042 | 1/2005 |

OTHER PUBLICATIONS

Selvaraj, V. et al., Biology of Reproduction, "Estrogenicity of the Isoflavone Metabolite Equol on Reproductive and Non-Reproductive Organs in Mice", vol. 71, pp. 966-972 (published May 2004).*
Ohta, Atsutane et al., "A Combination of Dietary Fructooligosaccharides and Isoflavone Conjugates Increases Femoral Bone Mineral Density and Equol Production in Ovariectomized Mice", J. Nutr., vol. 132, No. 7, pp. 2048-2054, (2002).
Johanna W. Lampe, et al., "Urinary Equol Excretion with a Soy Challenge: Influence of Habitual Diet" Proc Soc Exp Biol Med, vol. 217, No. 3, pp. 335-339 (1998).
Atsutane Ohta, et al., "A Combination of Dietary Fructooligosaccharides and Isoflavone Conjugates Increases Femoral Bone Mineral Density and Equol Production in Ovariectomized Mice", J. Nutr, vol. 132, pp. 2048-2054 (2002).
Akiko Tamura, et al., Summary of lectures of 2005 annual meeting of the Japanese Society for Bioscience Biotechnology and Agrochemistry, p. 97 (2005), with partial English translation.
Food Research Organization Information, No. 17, pp. 18-19 (2005), with partial English translation.
Tasleem A. Zafar, et al., "Inulin Effects on Bioavailability of Soy Isoflavones and Their Calcium Absorption Enhancing Ability", J. Agric. Food Chem, vol. 52, No. 10, pp. 2827-2831 (2004).
Karel Decroos, et al., "Isolation and characterisation of an equol-producing mixed microbial culture from a human faecal sample and its activity under gastrointestinal conditions", Arch Microbiol, vol. 183, No. 1, pp. 45-55 (2005).
Aki Tsukioka, "FANCL Confirms That Intake of Twintose Stimulates Isoflavone Activity", Internet Citation, Japan's Corporate News Network, XP-007914774, May 2, 2005, 1 page.
Hirokazu Tsuji, et al., "Isolation and characterization of the equol-producing bacterium *Slackia* sp. strain NATTS", Archives of Microbiology, vol. 192, No. 4, XP-019798341, Feb. 21, 2010, pp. 279-287.
Supplementary European Search Report issued Sep. 27, 2010, in European Patent Application No. 06822881.6.
U.S. Appl. No. 13/203,144, filed Aug. 24, 2011, Tsuji, et al.
Examination Report issued Jan. 10, 2013 in Australian Patent Application No. 2006309706.
G. M. Gaziev, et al., "Characteristics of *Klebsiella* strains isolated from patients with acute intestinal diseases", Zhurnal Mikrobiologii, i Immunobiologii, May 1986, (5), pp. 32-34 with English abstract and cover page.

(Continued)

*Primary Examiner* — Shaojia Anna Jiang
*Assistant Examiner* — Bahar Craigo
(74) *Attorney, Agent, or Firm* — Oblon, McClelland, Maier & Neustadt, L.L.P.

(57) ABSTRACT

An object of the invention is to provide a medical drug, a food and drink having a role in regulating the concentration of equol in vivo and being capable of taking for a long time with high safety and provide a selective medium for a microorganism having conversion ability to equol and a method of detecting the same. Provided are an equol concentration-raising or reducing agent containing a carbohydrate as an active ingredient; use of a carbohydrate for producing the equol concentration-raising or reducing agent; a method of raising or reducing the concentration of equol by administrating a carbohydrate in an effective dose; a selective medium containing a carbohydrate for a microorganism having conversion ability to equol; and a method of detecting a microorganism having conversion ability to equol by use of the selective medium.

21 Claims, 2 Drawing Sheets

(56) References Cited

OTHER PUBLICATIONS

P. Pohl, et al., "Selective citrate-adonitol medium for the isolation of various strains of *Escherichia coli* K99", Annales de Microbiologie (Paris), Jul.-Aug. 1984, 135B(1), pp. 29-33 with English abstract.

Kosaku Sakamoto, et al., "Growth inhibition and differentiation of HT-29 cells in vitro by inositol hexaphosphate (phytic acid)", Carcinogenesis, Sep. 1993, 14(9), pp. 1815-1819.

B.W. Senior, "Media for the detection and recognition of the enteropathogen *Providencia alcalifaciens* in faeces", J. Medical Microbiology, Jun. 1997, 46(6), pp. 524-527.

European Office Action in corresponding application No. 13004570.1, dated Feb. 5, 2014.

M. Furuse, et al., "Regulation of lipid metabolism by dietary sorbose in laying hens", Poultry Science, vol. 69, No. 9, Sep. 1, 1990, XP008166228.

R. Beyer, et al., "Reduced plasma cholesterol and lipoprotein in laying hens without concomitant reduction of egg cholesterol in response to dietary sorbose", Poultry Science, vol. 72, No. 1, Jan. 1, 1993, XP008166229.

A. Duncan, et al., "Premenopausal equol excretors show plasma hormone profiles associated with lowered risk of breast cancer", Cancer Epidemiology, vol. 9, Jan. 1, 2000. XP003024397.

\* cited by examiner

EQUOL LEVEL REGULATOR

TECHNICAL FIELD

The present invention relates to an equol concentration regulator, a selective medium for a microorganism having conversion ability to equol and a method of detecting the same.

BACKGROUND ART

Isoflavone rich in soybean food is known as a functional component effective in improving menopausal disorders such as malaise, preventing osteoporosis, preventing hyperlipidemia and arteriosclerosis, preventing breast cancer and prostate cancer and so on. Recent studies have revealed that one of the isoflavones called daidzein is metabolized in vivo by intestinal bacteria into equal, which has stronger estrogen action and antioxidation action. Equal has attracted attention as one of the important active ingredients performing the aforementioned actions in vivo.

In-vivo production of equol from daidzein is not equally performed in all humans and the production ability thereof varies between individuals. It has been reported that 30 to 50% of the humans have equol production ability (Non-Patent Document 1). By such the circumstances, research has been enthusiastically conducted for finding intestinal bacteria having equol production ability and substances accelerating production of equol. Microorganisms having equol production ability that have been so far reported are *Bacteroides ovatus, Streptococcus intermedius* and *Streptococcus constellatus* (Patent Document 1). It has been reported that an equol containing egg is obtained by giving a feed containing, e.g., daidzein and a soybean oligosaccharide to domestic fowls (Patent Document 2). A fructo-oligosaccharide (Non-patent Document 2) and twintose (R)(Non-Patent Document 3) have been reported to accelerate production of equol. Note that, Patent Document 1 discloses oligosaccharides such as lacto-oligosaccharide, soybean oligosaccharide, lacturose, lactitol, fructo-oligosaccharide and galacto-oligosaccharide as components contributing to survival and growth of microorganisms having equol production ability. However, each of these carbohydrates is mentioned simply as a nutritional component generally known to contribute to survival and growth of microorganisms; however, no mention is made of how these carbohydrates act upon equol production.

A substance exhibiting estrogen action in vivo is generally called an environmental hormone (endocrine disrupting chemical), which may be involved in reduction of sperm cells and reproduction capacity, and an increase in breast cancer occurrence concerning humans. Isoflavone and equol are each known as one of the phytoestrogens. Excessive intake and excessive in-vivo production of them are likely to have an adverse effect upon humans. Particularly when equol, which has estrogen activity several tens fold as high as other isoflavones, is excessively produced in vivo, it is important to suppress the production of equol. However, examples of microorganisms and substances capable of suppressing the production of equol that have been so far reported are *Lactobacillus gasseri* (Non-Patent Document 4), insulin (Non-Patent Document 5) and fructo-oligosaccharide (Non-Patent Document 6) alone.

Accordingly, it is very important to appropriately regulate the concentration of equol in-vivo in view of not only treating, improving or preventing various diseases as mentioned above but also avoiding adverse effects caused by the environment hormone-like action of equol. It has been therefore desired to develop a substance having a role in regulating the concentration of equol in vivo and capable of being taken for a long time with high safety.

However, microorganisms and substances capable of regulating the equol concentration in viva are only those mentioned above. Choices are extremely limited and their effects are insufficient. In addition, there have been no reports on a selective medium for a microorganism having conversion ability to equol. In the circumstances, it has been strongly desired to develop a selective medium for simply and quickly screening a microorganism having conversion ability to equol and detecting a microorganism having conversion ability to equol in a specimen.

[Patent Document 1] WO99/7392
[Patent Document 2] JP-A-2003-310177
[Non-Patent Document 1] Proc Soc Exp Biol Med, Vol. 217, No. 3, p 335-339 (1998)
[Non-Patent Document 2] J Nutr, Vol. 132, p 2048-2054 (2002)
[Non-Patent Document 3] Summary of lectures of 2005 annual meeting of the Japanese Society for Bioscience Biotechnology and Agrochemistry, p 97 (2005)
[Non-Patent Document 4] Food Research Organization Information, No. 17, p 18-19 (2005)
[Non-Patent Document 5] J Agric Food Chem, Vol. 52, No. 10, p 2827-2831 (2004)
[Non-Patent Document 6] Arch Microbiol, Vol. 183, No. 1, p 45-55 (2005)

DISCLOSURE OF THE INVENTION

Problems to be Solved by the Invention

Accordingly, an object of the present invention is to provide a medical drug and food and drink having a role in regulating the concentration of equol in vivo and capable of being taken for a long time with high safety, and to provide a selective medium for a microorganism having conversion ability to equol and a detection method thereof.

Means for Solving the Problems

The present inventors have conducted intensive studies with a view to attaining the aforementioned object. As a result, they found that various types of carbohydrates, which are safe substances widely taken as food for a long time, have a role in raising or reducing the concentration of equol. They further found that a microorganism having conversion ability to equol can be selectively grown in a medium containing a carbohydrate having a role in raising the concentration of equol. Based on the findings, the present invention was accomplished.

More specifically, according to the present invention, there is provided an equol concentration-raising agent comprising, as an active ingredient, at least one element selected from adonitol, arabinose, erythritol, galactose, lactitol, melezitose, trehalose, ribose, sorbose, xylose, inositol and sorbitol; use of at least one element selected from these carbohydrates for producing the equol concentration-raising agent; and a method of raising the concentration of equol characterized by administrating at least one element selected from these carbohydrates in an effective dose.

According to the present invention, there is further provided an equol concentration-reducing agent comprising, as an active ingredient, at least one element selected from glucose, lactose, lacturose, melibiose, raffinose, sucrose and galacto-oligosaccharide; use of at least one element selected from these carbohydrates for producing the equol concentration-reducing agent; and a method of reducing the concentration of equol characterized by administrating at least one element selected from these carbohydrates in an effective dose.

According to the present invention, there is further provided a selective medium for a microorganism having conversion ability to equol, comprising at least one element selected from adonitol, arabinose, erythritol, galactose, lactitol, melezitose, trehalose, ribose, sorbose, xylose, inositol and sorbitol.

According to the present invention, there is further provided a method of detecting a microorganism having conversion ability to equol in a specimen, comprising culturing the microorganism having conversion ability to equol contained in the specimen by using a selective medium containing at least one element selected from adonitol, arabinose, erythritol, galactose, lactitol, melezitose, trehalose, ribose, sorbose, xylose, inositol and sorbitol.

Effect of the Invention

Each carbohydrate to be used in the present invention has an excellent equol concentration-raising action or reducing action and is widely taken as food for a long time with high safety. Therefore, an equol concentration-raising agent or reducing agent according to the present invention can be daily used in safety for appropriately regulating the concentration of equol in vivo. Furthermore, use of a selective medium according to the present invention makes it possible to simply and quickly screen a microorganism having conversion ability to equol and detect the microorganism having conversion ability to equol in a specimen.

BEST MODE FOR CARRYING OUT THE INVENTION

Figure 1:
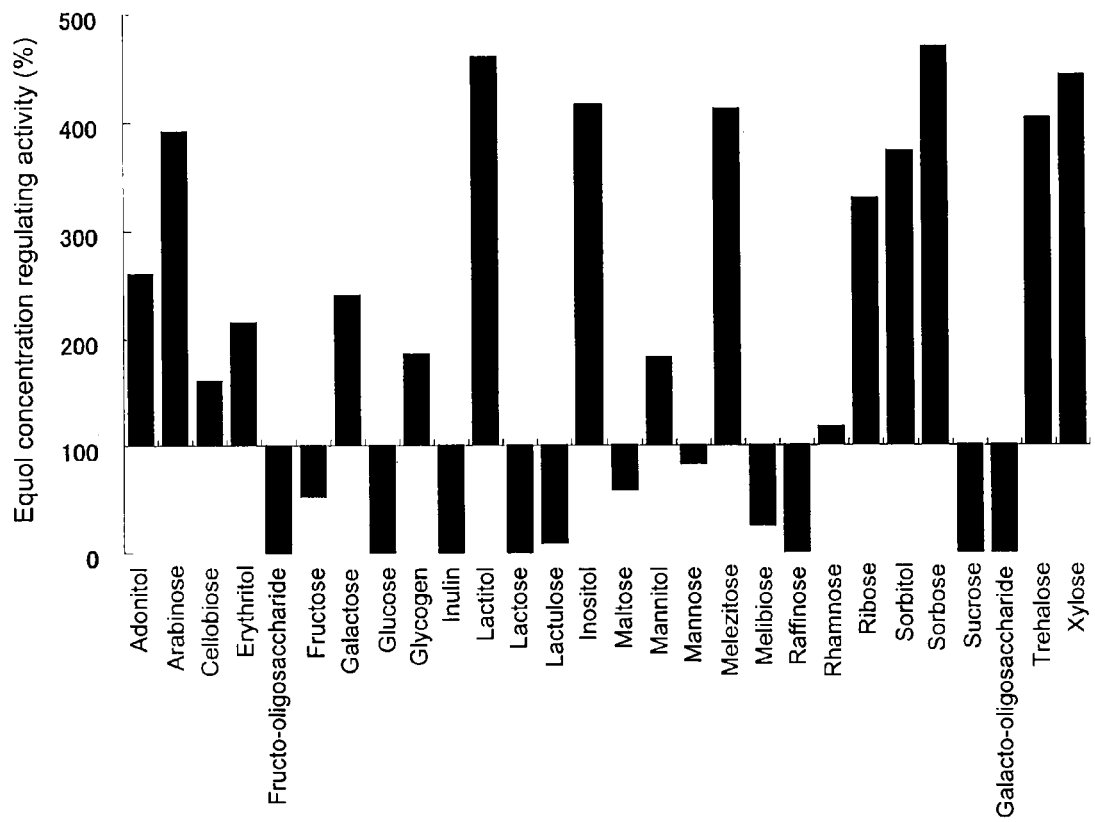
FIG. 1 is a graph showing the effects of carbohydrates upon conversion to equol.

Examples of the carbohydrate to be used in the present invention include adonitol, arabinose, erythritol, galactose, lactitol, melezitose, trehalose, ribose, sorbose, xylose, inositol, sorbitol, glucose, lactose, lacturose, melibiose, raffinose, sucrose and galacto-oligosaccharide. The carbohydrate may be D-form or L-form; however, preferably, D-form. Furthermore, an anhydride or a hydrate such as a 5 hydrate may be used.

Trehalose has $\alpha,\alpha$ isomer, $\alpha,\beta$ isomer and $\beta,\beta$ isomer, which differ in the manner of linkage between two glucose molecules. Although any one of these isomers can be used in the present invention, preferably, $\alpha,\alpha$ isomer is used.

Inositol to be used in the present invention has nine stereoisomers: myo-inositol, D(+)-inositol, L-(−)inositol, muco-inositol, scyll-inositol, cis-inositol, epi-inositol, allo-inositol and neo-inositol. Myo-inositol, D(+)-inositol, L-(−)inositol, muco-inositol and scyll-inositol are naturally occurring ones. However, myo-inositol is preferably used in view of availability. Two types or more of inositol stereoisomers may be used in combination.

The galacto-oligosaccharide to be used in the present invention is a general term referring to oligosaccharide having at least one galactose residue in a molecule. For example, a carbohydrate having 2 to 9 mono-carbohydrates linked to each other may be mentioned. Examples of the galacto-oligosaccharide include those galactose having a $\beta1$-2 linkage, $\beta1$-3 linkage, $\beta1$-4 linkage and $\beta1$-6 linkage; however, those having a $\beta1$-4 linkage and $\beta1$-6 linkage are particularly preferable. In the present invention, a mixture of these galacto-oligosaccharides can be used.

In the present invention, a commercially available carbohydrate such as a synthetic carbohydrate and a carbohydrate extracted from natural product may be used. Alternatively, natural occurring material rich in these carbohydrates may be used. More specifically, mention may be made of a material rich in adonitol such as a plant root and a riboflavin-containing material, a material rich in sorbose such as fruit, a material rich in melezitose such as honey or secreting fluid of plant and a material rich in trehalose such as mushroom.

The equol concentration regulating activity of a carbohydrate can be checked by taking feces from a human having ability to produce equol (equol producer), adding daidzein serving as a substrate for equol and a target carbohydrate to the feces thus taken, culturing the feces, determining the concentration of equol in the culture medium and fitting the determined equol concentration to the following equation in comparison with the concentration of equol in a culture medium containing no carbohydrate.

Equal concentration regulating activity (%)=(equol concentration of a culture medium containing a target carbohydrate)/(equol concentration of a culture medium containing no carbohydrate)×100

The feces taken from the equol producer are preferably washed by centrifugation for use. Culture is desirably performed in anaerobic conditions in order to reproduce the state within the human intestinal tract. The concentration of equol can be determined in accordance with a customary method such as liquid chromatography or LC-MS. A carbohydrate having an equol concentration-raising action according to the present invention is one having an equol concentration regulating activity of 200% or more, and particularly preferably, 400% or more. Furthermore, a carbohydrate having an equol concentration-reducing action according to the present invention is one having an equol concentration regulating activity of 50% or less, and particularly preferably, 10% or less.

When the feces taken from an equol producer are anaerobically cultured after adding daidzein and an antibiotic thereto, production of equol from daidzein is inhibited. From this, it is considered that the equol concentration regulating actions of carbohydrates may be mediated by microorganisms present in the feces. More specifically, it is estimated that a carbohydrate having an equol concentration-raising action selectively accelerates growth of a microorganism having conversion ability to equol or enhances the conversion ability to equol of the microorganism; whereas, a carbohydrate having an equol concentration-reducing action selectively inhibits growth of a microorganism having conversion ability to equol or interferes with the conversion ability to equol of the microorganism.

A medium containing a carbohydrate having an equol concentration-raising action can be used as a selective medium for a microorganism having conversion ability to equol. The selective medium contains at least one element selected from adonitol, arabinose, erythritol, galactose, lactitol, melezitose, trehalose, ribose, sorbose, xylose, inositol and sorbitol. Other than these carbohydrates, daidzein serving as a substrate for equol is preferably contained. A medium can be used as long as it contains a carbohydrate, for example, in an amount of 0.3 to 3% by mass and daidzein in an amount of 0.0025 to 0.25% by mass relative to the total amount of the medium in a usable state. Examples of the medium to be used herein include not only a medium that can be immediately used for culturing but also a mixture of medium constituent components except water to be subjected to culture after dissolving in water and sterilizing it. The medium can be used as a liquid medium or a solid medium resulted from adding agar or the like thereto. An antibiotic may be added to the medium in order to increase selectivity of a target microorganism. Colistin and chloramphenicol may be added, for example, in an amount of 1 to 100 μg/ml relative to the total amount of the medium in a usable state. Furthermore, an appropriate component (other than those mentioned above) such as a nitrogen source may be added. However, it is not preferable to use a component that inhibits growth of a microorganism having conversion ability to equol and interferes with the conversion ability to equol of a microorganism. Examples of the component that can be added include peptone, trypticase peptone, yeast extract, hemin, vitamin such as vitamin K1, L-cysteine hydrochloride, $KH_2PO_4$, $K_2HPO_4$, NaCl, $(NH_4)_2SO_4$, $CaCl_2$ and $MgSO_4$. A composition of the medium according to the present invention except for a carbohydrate having an equol concentration-raising action and daidzein may be the same as that of PY medium, GAM medium or BHI medium.

A microorganism having equol production ability (daidzein-to-equol conversion) can be screened and obtained by sub-culturing a specimen such as feces in the selective medium while confirming equol conversion ability from daidzein. In addition, a microorganism having conversion ability to equol present in a specimen can be detected by use of the selective medium. A microorganism having conversion ability to equol can be detected, for example, by culturing a specimen in the medium according to the present invention and determining the concentration of equol in the medium. At this time, if the concentration of equol increases, a microorganism having equol production ability is determined to be present in the specimen. In this case, as a control for determining an increase of equol concentration, the medium containing the same components except for a carbohydrate according to the present invention may be used.

A specimen for use in a detection method according to the present invention is not particularly limited. However, when a microorganism having conversion ability to equol is screened, a specimen supposed to contain a microorganism having conversion ability to equol is desirably used. In particular, specimens such as feces and content of the digestive tract are preferably used.

The carbohydrate having an equol concentration-raising action according to the present invention (adonitol, arabinose, erythritol, galactose, lactitol, melezitose, trehalose, ribose, sorbose, xylose, inositol or sorbitol) can be used as an equol concentration-raising agent in the body, blood and intestine such as large intestine. The equol concentration-raising agent containing the carbohydrate as an active ingredient can be used, for example, for treating, improving or preventing various types of diseases in which isoflavone plays a part including menopausal disorders such as malaise, osteoporosis, hyperlipidemia, arteriosclerosis, breast cancer, prostate cancer and premenstrual syndrome. The carbohydrate having an equol concentration-raising action according to the present invention may be used alone or in combination with two or more types.

Furthermore, the carbohydrate according to the present invention is preferably used in combination with daidzein serving as a substrate for equol. A commercially available daidzein such as synthesized daidzein and daidzein extracted from a natural product may be used. Alternatively, naturally occurring material rich in daidzein and a processed product thereof may be used. Specific examples of the material rich in daidzein include soybean, pea, kudzu and crowbar. Examples of the processed product thereof include tofu, soybean milk, fried bean curd, fermented soybeans, soy sauce, soybean paste and tempeh. Furthermore, an isoflavone glycoside is generally converted into an aglycone by the action of intestinal bacterium in vivo. Therefore, glycoside-compounds of daidzein such as daidzin, malonyldaidzin and acetyldaidzin may be used.

The carbohydrate according to the present invention may be used in combination with a microorganism having conversion ability to equol and obtained in the selective medium according to the present invention. When the microorganism is used, the form of the microorganism is not particularly limited. Living bacteria, inactivated bacteria with heat (dead bacteria) or lyophilized bacteria may be used. Alternatively, cultured products containing these bacteria may be used.

The carbohydrate having an equol concentration-reducing action according to the present invention (glucose, lactose, lacturose, melibiose, raffinose, sucrose or galacto-oligosaccharide) can be used as an equol concentration-reducing agent in the body, blood and intestine such as large intestine. The equol concentration-reducing agent containing the carbohydrate as an active ingredient can be used for preventing adverse effects such as reduction of sperm cells and reduction of reproductive capacity caused by an environmental hormone like action of equol. The carbohydrate having an equol concentration-reducing action of the present invention may be used alone or in combination with two or more types.

Appropriate use of the equol concentration-raising agent and the equol concentration-reducing agent according to the present invention enables to appropriately regulate the concentration of equol in vivo. For example, the equol concentration-reducing agent according to the present invention may be applied to infants, young children and pregnant women, who are said to be highly sensitive to environmental hormones, in order to reduce a risk of exposure to equol. Conversely, the equol concentration-raising agent according to the present invention may be applied to the middle aged and advanced aged persons, who have a high risk of menopausal disorders such as malaise, osteoporosis and cancer. It is very important for a person who has no ability to produce equol (non-equol producer) and a person who has less ability to produce equol to use an equol concentration-raising agent on a daily basis in view of prevention of various diseases in which isoflavone plays a part. Whether a target person has ability to produce equol in vivo or not can be checked by measuring the concentration of equol in the urine or blood of the person by a customary method such as HPLC.

The carbohydrate according to the present invention serving as an active ingredient of the equol concentration-raising agent or the equol concentration-reducing agent has been widely used as food for a long time with high safety. Therefore, the dose of the carbohydrate to be used in the equol concentration-raising agent or the equol concentration-reducing agent is not strictly limited. However, it is desirable to specify an appropriate dose since the obtained effect varies depending upon various conditions in use such as persons and diseases to which the agent is applied. The dose thereof is 0.1 mg to 100 g per day and particularly preferably 50 mg to 50 g.

The equol concentration-raising agent and the equol concentration-reducing agent according to the present invention may be administered orally or non-orally; however, oral administration is preferable. The agent can be administered as a common pharmaceutical preparation by blending a carbohydrate serving as an active ingredient with a solid or liquid pharmaceutically nontoxic carrier suitable for administration manner such as oral or intrarectal administration or injection.

Examples of such a preparation include solid agents such as tablets, granules, powder and encapsulated agents; liquid agents such as a solution, suspension and emulsion, and freeze-dried agents. These preparations can be obtained by customary pharmaceutical means. Examples of the pharmaceutically nontoxic carrier include starch, dextrin, fatty acid glyceride, polyethylene glycol, hydroxyethyl starch, ethylene glycol, polyoxyethylene sorbitan fatty acid ester, amino acids, gelatin, albumin, water and saline. Furthermore, if necessary, customarily used additives such as a stabilization agent, a wetting agent, an emulsifying agent, a binder, an isotonization agent, an excipient may be added.

The carbohydrate according to the present invention may be used not only as a pharmaceutical preparation as described above but also as food and drink. In this case, the carbohydrate according to the present invention may be contained as it is in food and drink or together with various types of nutritional components. A carbohydrate having an equol concentration-raising action can be used as a health food or food material useful for raising the concentration of equol in vivo or improving and preventing menopausal disorders such as malaise, osteoporosis, hyperlipidemia, arteriosclerosis, breast cancer, prostate cancer and premenstrual syndrome. To the food and drink or the containers thereof, a label informing the aforementioned effect of the products may be attached. A carbohydrate having an equol concentration-reducing action can be used as a health food or food material useful for reducing the concentration of equol in vivo or preventing reduction of sperm cells and reproductive capacity caused by an environmental hormone like action of equol. To the food and drink or the containers thereof, a label informing the aforementioned effect of the products may be attached. When a carbohydrate according to the present invention is blended with food and drink, the carbohydrate may be molded into edible form such as granules, particles, tablets, capsules and paste by customary means with the addition of appropriate additives available for food and drink. Alternatively, the carbohydrate can be added to various types of foods such as processed meat products such as ham and sausage, processed fish products such as fish minced and steamed food and tubular fish meat, bread, confection, butter, powdered milk, fermented dairy products and can be added to drinks such as water, fruit juice, milk, soft drinks and tea drinks. Note that animal feed is included in food and drink.

EXAMPLES

The present invention will be explained more specifically by way of Experimental Examples and Examples. However, the present invention is not limited to these.

Experimental Example 1

Effect of Carbohydrates Upon Equol Production

Fresh feces of an equol producer were suspended in a dilute solution (10-fold by volume) containing 0.00255% of $KH_2PO_4$, 0.00255% of $K_2HPO_4$, 0.006% of NaCl, 0.002556 of $(NH_4)_2SO_4$, 0.000255% of $CaCl_2$, 0.000255% of $MgSO_4$, 0.1% of a 0.1% resazurin solution, 2.2% of an 8% $Na_2CO_3$ solution and 0.05% of L-cysteine hydrochloride by use of glass beads (φ 3 mm) in anaerobic conditions and solid matter was removed by use of sterilized gauze. The solution was centrifuged at 8,000 rpm for 10 minutes. Precipitation was suspended in a dilute solution in the same amount thereof. The solution was stored in a freezer at −30° C. as it was.

The feces dilution solution was thawed and centrifuged again. Precipitation was resuspended in PY medium (100-fold by volume) containing 0.5% of peptone, 0.5% of trypticase peptone, 1% of yeast extract, 0.00005% of hemin, 0.0001% of vitamin K1, 0.05% of L-cysteine hydrochloride, 0.0006% of $KH_2PO_4$, 0.0006% of $K_2HPO_4$, 0.0012% of NaCl, 0.0006% of $(NH_4)_2SO_4$, 0.00006% of $CaCl_2$ and 0.00006% of $MgSO_4$. At this time, adonitol, arabinose, cellobiose, erythritol, fructo-oligosaccharide, fructose, galactose, glucose, glycogen, inositol, insulin, lactitol, lactose, lactulose, maltose, mannitol, mannose, melezitose, melibiose, raffinose, rhamnose, ribose, sorbitol, sorbose, sucrose, trehalose, xylose, or galacto-oligosaccharide was added so as to obtain a final concentration of 1%. Simultaneously, a series of sample containing no carbohydrate was prepared. To the series of samples, daidzein was added so as to obtain a final concentration of 100 µM. Culture was performed in completely anaerobic conditions at 37° C. for 16 hours. Note that culture was performed independently in four series. From the culture solution obtained, daidzein and equol were extracted and subjected to HPLC analysis. Note that inositol used herein is myo-inositol manufactured by SIGMA and glycogen was one derived from oyster and manufactured by SIGMA. Trehalose is D(+) trehalose (α,α form) manufactured by SIGMA and galacto-oligosaccharide is TOS-S, which is a mixture of 4'galactosyl-lactose and 6'galactosyl-lactose, and manufactured by Yakult Pharmaceutical Industry Co., Ltd. Fructo-oligosaccharide is a mixture of 1-kestose, nystose and 1-fructosyl-D-nystose manufactured by Wako Pure Chemical Industries, Ltd.

Daidzein and equol were extracted by the following manner. To 500 µL of a culture solution, 250 µL of diethyl ether was added and sufficiently stirred. The solution mixture was centrifuged at 2,000 rpm for 10 minutes to obtain a diethyl ether layer. The remaining aqueous layer was subjected to diethyl ether extraction performed in the same manner. The ether layers obtained in the two extraction operations were combined, concentrated and dried under spray of nitrogen gas flow at 40° C. The dried product was dissolved in 250 µL of 80% methanol and filtrated through a filter to obtain a sample to be subjected to measurement.

Furthermore, HPLC was performed in the following conditions:

Apparatus: LC module 1 (Waters)
Column: YMC-Pack CN (manufactured by Y.M.C.)
Detection: Ultraviolet absorption photometer (determined at a wavelength of 280 nm)
Column temperature: 40° C.
Mobile phase: solution mixture of 0.1% formic acid solution/acetonitrile/methanol (87:3:10)
Flow amount: 2.5 mL/min
Injection amount of sample: 10 µL Daidzein and equol standard products were poured in the aforementioned conditions to form calibration curves, respectively. In this manner, daidzein and equol concentrations of the samples were determined. Based on the concentrations thus obtained, and in accordance with the equation shown in paragraph [0020], equol concentration regulating activity was calculated.

The results are shown in Table 1 and FIG. 1. Assuming that the daidzein-to-equol conversion rate of a sample containing no carbohydrate exhibited 100%, an daidzein-to-equol conversion rate was suppressed to 50% or less in each of the samples containing fructo-oligosaccharide, glucose, insulin, lactose, lactulose, melibiose, raffinose, sucrose and galacto-oligosaccharide. From this, it was found that these carbohydrates have negative equol concentration regulating activities. In particular, in each case of fructo-oligosaccharide, glucose, insulin, lactose, raffinose, sucrose and galacto-oligosaccharide, equol production was not observed and 100 μM of daidzein added to the medium mostly remained. Note that it is known that insulin reduces the equol concentration in the serum of a rat (Non-Patent Document 5). In this test system, it was found that insulin significantly decreases the conversion rate of daidzein-to-equol. On the other hand, it is reported that fructo-oligosaccharide accelerates the production of equol (Non-Patent Document 5), whereas it reduces the equol production activity of cultured human feces (Non-Patent Document 6). However, in this test system, fructo-oligosaccharide was found to significantly reduce the daidzein-to-equol conversion rate from daidzein.

On the other hand, in each case of adonitol, arabinose, erythritol, galactose, lactitol, melezitose, trehalose, ribose, sorbose, xylose, inositol and sorbitol, the daidzein-to-equol conversion rate was significantly increased to 200% or more. From this, it was found that these carbohydrates have positive equol concentration regulating activities. In particular, in the cases of lactitol, melezitose, trehalose, sorbose, xylose and inositol, 70% or more of 100 μM daidzein added to the medium were converted into equol. The equol concentration regulating activities were 400% or more.

TABLE 1

Effect of carbohydrate upon daidzein-to-equol conversion

| Type of carbohydrate | Equol concentration in medium (μM) | Equol concentration regulating activity (%) |
|---|---|---|
| Adonitol | 47.0 | 260.0 |
| Arabinose | 70.6 | 391.1 |
| Cellobiose | 29.0 | 160.6 |
| Erythritol | 38.7 | 214.2 |
| Fructo-oligosaccharide | 0.0 | 0.0 |
| Fructose | 9.3 | 51.5 |
| Galactose | 65.0 | 240.1 |
| Glucose | 0.0 | 0.0 |
| Glycogen | 33.4 | 184.8 |
| Inulin | 0.0 | 0.0 |
| Lactitol | 82.9 | 459.1 |
| Lactose | 0.0 | 0.0 |
| Lactulose | 1.5 | 8.1 |
| Inositol | 75.2 | 416.2 |
| Maltose | 10.6 | 58.5 |
| Mannitol | 32.9 | 182.2 |
| Mannose | 15.0 | 83.0 |
| Melezitose | 74.3 | 411.6 |
| Melibiose | 4.5 | 24.8 |
| Raffinose | 0.0 | 0.0 |
| Rhamnose | 21.0 | 116.4 |
| Ribose | 59.5 | 329.6 |
| Sorbitol | 67.3 | 372.5 |
| Sorbose | 84.5 | 467.7 |
| Sucrose | 0.0 | 0.0 |
| Galacto-oligosaccharide | 0.0 | 0.0 |
| Trehalose | 72.9 | 403.5 |
| Xylose | 79.9 | 442.6 |
| No carbohydrate | 18.1 | 100.0 |

Experimental Example 2

Culture of Microorganism Having Conversion Ability to Equol

A feces suspension solution stored in the process according to Experimental Example 1 was added to 500 μL of PY mediums (to which adonitol or sorbose was previously added so as to obtain a final concentration of 1%; and distilled water was added in place of adonitol or sorbose for preparing a control sample) so as to obtain a content of 1/10 and daidzein was added so as to obtain a final concentration of 100 μM. Each medium was cultured at 37° C. for 16 hours in completely anaerobic conditions. After the culturing, an aliquot of 50 μL was taken from the culture solution and transferred to a fresh PY medium (500 μL). The remaining culture solution was subjected to daidzein and equol extraction. Thereafter, the same operation was repeatedly performed. In this manner, sub-culture was performed. At this time, a bacterial solution was appropriately subjected to gram staining and microscopically observed. The extraction of daidzein and equol, and quantification by HPLC were performed in accordance with the method described in Experimental Example 1. Each obtained daidzein and equol concentration was fitted into the following formula to obtain a daidzein-to-equol conversion rate. Note that culture was performed independently in three series to obtain an average conversion rate and standard deviation thereof.

Daidzein-to-equol conversion rate (%)=100×(equol concentration of culture solution)/(addition of equol concentration and daidzein concentration of culture solution)

Figure 2:
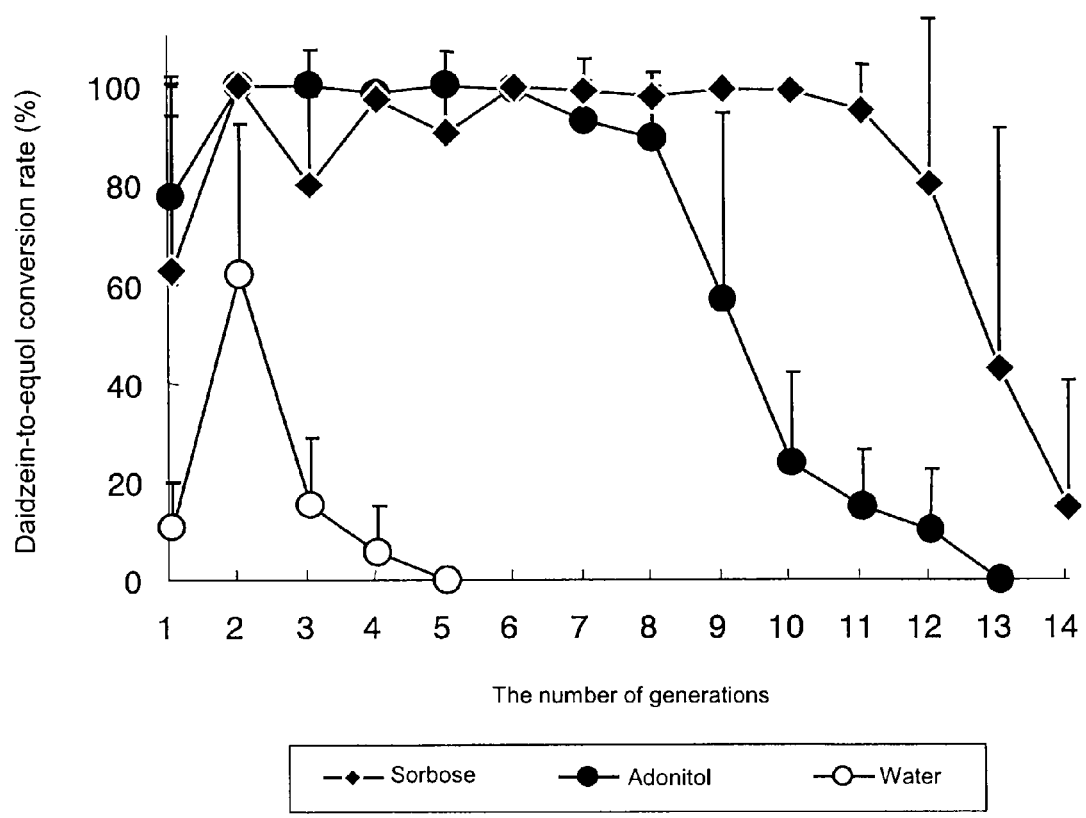
FIG. 2 is a graph showing the daidzein-to-equol conversion rate in sub-culturing feces of an equol producer in a selective medium.

As a result, as shown in FIG. 2, in each case where adonitol or sorbose was used as carbohydrate sources, conversion ability to equol can be maintained to the 8th generation and 11th generation, respectively. Furthermore, since original feces are only contained in a fraction of $10^{12}$ in the culture solution of the 11th generation, it was estimated that conversion ability to equol could be maintained only in PY medium containing sorbose as a carbohydrate source. On the other hand, when a gram stained image of bacteria of the 11th generation sub-cultured in PY medium containing sorbose as a carbohydrate source was observed, 3 to 5 types of bacteria were determined. From this, daidzein-to-equol conversion bacteria were found to selectively grow in the sub-culture of the 11th generation.

Formulation Example 1

Production of Tablets

The following components were mixed in accordance with the following formula, granulated, dried, sized and made into tablets.

| (Formula) | (mg) |
|---|---|
| Microcrystalline cellulose | 100 |
| Trehalose | 80 |
| Magnesium stearate | 0.5 |
| Methylcellulose | 12 |

Formulation Example 2

Production of Soft Drink

The components were mixed by a customary method in accordance with the following formula and homogenized to obtain a soft drink. A brown bottle was charged with the obtained soft drink, sealed with an aluminum cap and subjected to heat treatment.

| (Formula) | (g) |
| --- | --- |
| Flavor | 0.8 |
| Citric acid | 0.2 |
| Fructose | 4 |
| Galacto-oligosaccharide | 1.5 |
| Water | 93.5 |

Formulation Example 3

Preparation of Medium

The components were mixed in accordance with the following formula, adjusted to 1 L with water and sterilized to prepare a selective medium for a microorganism having daidzein-to-equol conversion ability.

| (Formula) | (g) |
| --- | --- |
| Peptone | 5 |
| Trypticase peptone | 5 |
| Yeast extract | 10 |
| Adonitol | 10 |
| Sorbose | 10 |
| Hemin | 0.0005 |
| Vitamin K1 | 0.001 |
| L-cysteine hydrochloride | 0.5 |
| $KH_2PO_4$ | 0.006 |
| $K_2HPO_4$ | 0.006 |
| NaCl | 0.012 |
| $(NH_4)_2SO_4$ | 0.006 |
| $CaCl_2$ | 0.0006 |
| $MgSO_4$ | 0.0006 |
| 10 mM daidzein solution | 10 |

The invention claimed is:

1. A method of raising the concentration of equol in a subject, comprising:
   administering to an equol-producing subject selected from the group consisting of a subject having a menopausal disorder, malaise, premenstrual syndrome, osteoporosis, hyperlipidemia, arteriosclerosis, breast cancer and prostate cancer,
   daidzein and an effective dose of an agent comprising at least one compound selected from the group consisting of adonitol, arabinose, erythritol, galactose, melezitose, ribose, sorbose, xylose, and inositol; wherein said agent excludes a microorganism that converts daidzein into equol;
   wherein the feces of said subject contain equol-producing bacteria, and
   wherein said dose is effective to raise the concentration of equol in the subject compared to the untreated subject.

2. The method of claim 1, wherein said subject has a disease or disorder selected from the group consisting of a menopausal disorder, malaise, or premenstrual syndrome.

3. The method of claim 1, wherein said subject has a disease or disorder selected from the group consisting of osteoporosis, hyperlipidemia, and arteriosclerosis.

4. The method of claim 1, wherein said subject has a disease or disorder selected from the group consisting of breast cancer and prostate cancer.

5. The method of claim 1, wherein said subject is human.

6. The method of claim 1, wherein said at least one compound, which is selected from the group consisting of adonitol, arabinose, erythritol, galactose, melezitose, ribose, sorbose, xylose, and inositol, is administered simultaneously with daidzein.

7. The method of claim 1, wherein said at least one compound, which is selected from the group consisting of adonitol, arabinose, erythritol, galactose, melezitose, ribose, sorbose, xylose, and inositol, is administered separately from daidzein.

8. The method of claim 1, wherein said at least one compound is selected from the group consisting of adonitol, erythritol, galactose, ribose, sorbose, and inositol.

9. The method of claim 1, wherein said effective dose of said compound in the agent ranges from 0.1 mg to 100 gr per day.

10. The method of claim 1, wherein said effective dose of said compound in the agent ranges from 50 mg to 50 gr per day.

11. The method of claim 1, wherein said agent is administered orally.

12. The method of claim 1, wherein said agent is administered non-orally.

13. The method of claim 1, wherein said compound is adonitol.

14. The method of claim 1, wherein said compound is arabinose.

15. The method of claim 1, wherein said compound is erythritol.

16. The method of claim 1, wherein said compound is galactose.

17. The method of claim 1, wherein said compound is melezitose.

18. The method of claim 1, wherein said compound is ribose.

19. The method of claim 1, wherein said compound is sorbose.

20. The method of claim 1, wherein said compound is xylose.

21. The method of claim 1, wherein said compound is inositol.

* * * * *